United States Patent [19]

Narasaka et al.

[11] Patent Number: 5,250,697
[45] Date of Patent: Oct. 5, 1993

[54] CYCLOBUTANE DERIVATIVES

[75] Inventors: Koichi Narasaka; Yujiro Hayashi, both of Tokyo, Japan

[73] Assignee: Nippon Kayaku Kabushiki Kaisha, Tokyo, Japan

[21] Appl. No.: 657,463

[22] Filed: Feb. 19, 1991

[30] Foreign Application Priority Data

Mar. 1, 1990 [JP] Japan .................. 2-47168
Mar. 23, 1990 [JP] Japan .................. 2-72024

[51] Int. Cl.$^5$ .......................................... C07D 263/04
[52] U.S. Cl. ................................................ 548/230
[58] Field of Search ................................... 548/230

[56] References Cited

FOREIGN PATENT DOCUMENTS 0358154 3/1990 European Pat. Off. .

OTHER PUBLICATIONS

Chemistry Letters, No. 5, 1989, pp. 793-976, Tokyo, Japan, Y. Hayashi, et al.
Chemistry Letters, No. 8, Aug. 1990, pp. 1295-1298, Tokyo, Japan, Y. Hayashi et al.

*Primary Examiner*—Robert W. Ramsuer
*Assistant Examiner*—Joseph K. McKane
*Attorney, Agent, or Firm*—Nields & Lemack

[57] ABSTRACT

Cyclobutane derivatives represented by the following general formula (I):

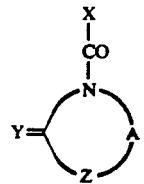

(I)

wherein X represents a group represented by the formula

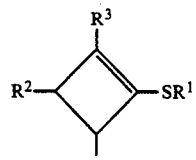

or the formula

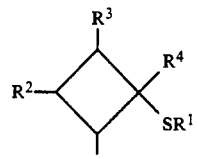

which is expected to be useful as reagents, drugs, agricultural chemicals and perfumes as well as an intermediate for the preparation thereof.

3 Claims, No Drawings

CYCLOBUTANE DERIVATIVES

FIELD OF THE INVENTION

This invention relates to a novel cyclobutane derivative which is expected to be useful as reagents, drugs, agricultural chemicals, and perfumes as well as an intermediate for preparing them.

BACKGROUND OF THE INVENTION

A cyclobutane derivative compound (IV), which is expected to be useful as an antiviral drug, may be synthesized by, for example, the following method (refer to EP-A-358154).

[Reaction scheme 1]

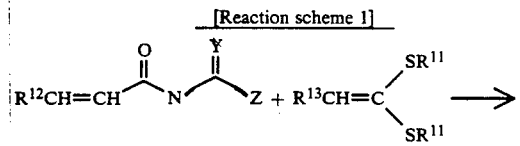

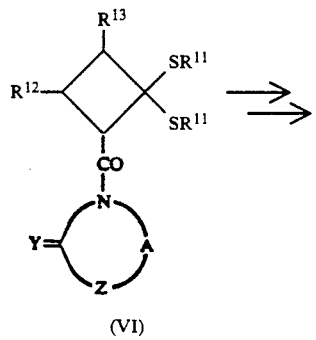

(VI)

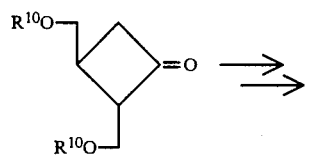

(VII)

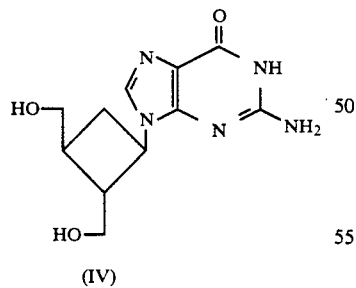

(IV)

wherein $R^{10}$ represents a hydrogen atom or a protecting group; $R^{11}$ represents an alkyl group having 1 to 5 carbon atoms, an aralkyl group or a cyclic alkylene group having 2 or 3 carbon atoms which is formed by binding two $R^{11}$ groups to each other;

$R^{12}$ represents a hydrogen atom, an alkyl group having 1 to 5 carbon atoms, a protected hydroxyalkyl group having 1 to 5 carbon atoms or a protected carboxyl group;

$R^{13}$ represents a hydrogen atom, an alkyl group having 1 to 5 carbon atoms, an alkoxy group having 1 to 5 carbon atoms or an aralkyloxy group;

A represents a straight-chain or a branched alkylene group having 2 to 5 carbon atoms;

Y represents an oxygen or a sulfur atom; and

Z represents an optionally substituted methylene group or an oxygen or a sulfur atom.

However the aforesaid reaction comprising reacting a compound represented by the general formula (II) with a compound represented by the general formula (V) to thereby give a compound represented by the general formula (VI) cannot smoothly proceed unless the $R^{13}$ group in the compound of the general formula (V) is a hydrogen atom. Further, the compound of the general formula (VI) thus obtained should be carefully handled since it is relatively unstable to acids.

Cyclobutane derivatives and condensed ring compounds having a cyclobutane ring are useful as drugs, agricultural chemicals, perfumes as well as starting materials and intermediates for the preparation thereof. However it is difficult to produce these cyclobutane derivatives and condensed ring compounds having a cyclobutane ring. In particular, no practical process has been known hitherto for preparing these compounds which are optically active.

SUMMARY OF THE INVENTION

The present invention relates to a cyclobutane derivative represented by the following general formula (I):

(I)

wherein X represents a group represented by the formula

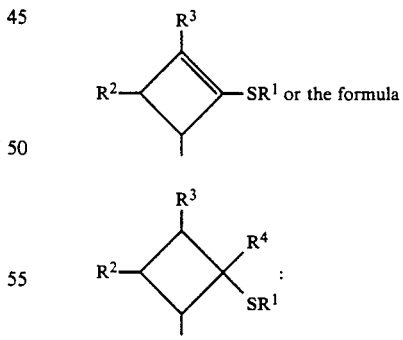

(wherein $R^1$ represents an alkyl group having 1 to 5 carbon atoms or an aryl-substituted alkyl group wherein the alkyl group has 1 to 5 carbon atoms; $R^2$ represents a hydrogen atom, an alkyl group having 1 to 5 carbon atoms, a protected hydroxyalkyl group having 1 to 5 carbon atoms or a protected carboxyl group; and $R^3$ and $R^4$ independently represent each a hydrogen atom, an alkyl group having 1 to 5 carbon atoms, a protected hydroxyalkyl group having 1 to 5 carbon atoms, an alkoxy group having 1 to 5 carbon atoms or an aryl-substituted alkoxy group wherein the alkoxy group has 1 to 5 carbon atoms; or alternately $R^3$ and $R^4$ are bound together to thereby form a 3- to 30-membered carbocyclic or heterocyclic ring);

A represents an optionally substituted polymethylene group having 2 to 5 carbon atoms;

Y represents an oxygen or a sulfur atom; and Z represents an optionally substituted methylene group or an oxygen or a sulfur atom.

DETAILED DESCRIPTION OF THE INVENTION

Among compounds represented by the general formula (I), examples of those wherein X represents a

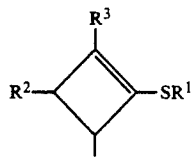

group are as follows.

In the present specification, the relative configuration of a compound is given in such a manner that when the cyclobutane ring is assumed to be on a plane, a substituent located below (one side) said plane is expressed by α, whereas a substituent located above (another side) of said plane is expressed by β.

1-1. (3R,4R)-3-methoxycarbonyl-1-methylthio-4-(oxazolidin-2-on-3-yl)carbonyl-1-cyclobutene;
1-2. (3S,4S)-3-methoxycarbonyl-1-methylthio-4-(oxazolidin-2-on-3-yl)carbonyl-1-cyclobutene;
1-3. (±)-(3β, 4α)-3-methoxycarbonyl-1-methylthio-4-(oxazolidin-2-on-3-yl)carbonyl-1-cyclobutene;
1-4. (3S,4R)-2-butyl-3-methoxycarbonyl-1-methylthio-4-(oxazolidin-2-on-3-yl)carbonyl-1-cyclobutene;
1-5. (3R,4S)-2-butyl-3-methoxycarbonyl-1-methylthio-4-(oxazolidin-2-on-3-yl)carbonyl-1-cyclobutene;
1-6. (±)-(3β, 4α)-2-butyl-3-methoxycarbonyl-1-methylthio-4-(oxazolidin-2-on-3-yl)carbonyl-1-cyclobutene;
1-7. (3S,4R)-3-methoxycarbonyl-2-methyl-1-methylthio-4-(oxazolidin-2-on-3-yl)carbonyl-1-cyclobutene;
1-8. (3R,4S)-3-methoxycarbonyl-2-methyl-1-methylthio-4-(oxazolidin-2-on-3-yl)carbonyl-1-cyclobutene;
1-9. (±)-(3β, 4α)-3-methoxycarbonyl-2-methyl-1-methylthio-4-(oxazolidin-2-on-3-yl)carbonyl-1-cyclobutene;
1-10. (4R)-2-butyl-1-methylthio-4-(oxazolidin-2-on-3-yl)carbonyl-1-cyclobutene;
1-11. (4S)-2-butyl-1-methylthio-4-(oxazolidin-2-on-3-yl)carbonyl-1-cyclobutene;
1-12. (±)-2-butyl-1-methylthio-4-(oxazolidin-2-on-3-yl)carbonyl-1-cyclobutene;
1-13. (4R)-2-methyl-1-methylthio-4-(oxazolidin-2-on-3-yl)carbonyl-1-cyclobutene;
1-14. (4S)-2-methyl-1-methylthio-4-(oxazolidin-2-on-3-yl)carbonyl-1-cyclobutene;
1-15. (±)-2-methyl-1-methylthio-4-(oxazolidin-2-on-3-yl)carbonyl-1-cyclobutene;
1-16. 4-(4-isopropyloxazolidin-2-on-3-yl)carbonyl-3-methoxycarbonyl-1-methylthio-1-cyclobutene; and
1-17. 4-(4-methyl-5-phenyloxazolidin-2-on-3-yl)-carbonyl-3-methoxycarbonyl-1-methylthio-1-cyclobutene.

Each compound given above may be obtained by cyclocondensing a compound represented by the general formula (II):

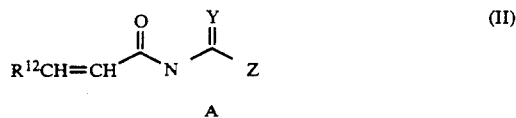

wherein $R^2$ represent a hydrogen atom, an alkyl group having 1 to 5 carbon atoms, a protected hydroxyalkyl group having 1 to 5 carbon atoms or a protected carboxyl group;

A represents an optionally substituted polymethylene group having 2 to 5 carbon atoms;

Y represents an oxygen or a sulfur atom; and

Z represents an optionally substituted methylene group or an oxygen or a sulfur atom; with a compound represented by the general formula (1-III):

wherein $R^1$ represents an alkyl group having 1 to 5 carbon atoms or an aryl-substituted alkyl group;

$R^3$ represents a hydrogen atom, an alkyl group having 1 to 5 carbon atoms, a protected hydroxyalkyl group having 1 to 5 carbon atoms, an alkoxy group having 1 to 5 carbon atoms or an aryl-substituted alkoxy group wherein the alkoxy group has 1 to 5 carbon atoms.

When the compound of the general formula (II) is reacted with the compound of the general formula (1-III) with the use of a condensation catalyst, an optically active cyclobutane compound represented by the general formula (I) or a racemic modification thereof may be obtained, depending on the employed catalyst, at a high yield. As the condensation catalyst to be used in this reaction, a Lewis acid or a combination of a Lewis acid with an equivalent or excessive amount of a ligand may be cited. Examples of the Lewis acid include titanium compounds such as titanium tetrachloride and dichlorodiisopropoxy-titanium, tin compounds such as tin (II) dichloride, tin (IV) tetrachloride and stannous triflate, and aluminum compounds such as dimethylaluminum chloride and diethylaluminum chloride. Preferable examples of the ligand include sterically hindered diols such as those having an at least 5-(preferably 5- to 8-) membered ring, to both sides of which hydroxylated groups are bound, in the molecule, for example, (2S,3S)-2,3-O-(1-phenylethylidene)-1,1,4,4-tetraphenyl-1,2,3,4-butanetetraol (compound A), (2R,3R)-2,3-O-(1-phenylethylidene)-1,1,4,4-tetraphenyl-1,2,3,4-butanetetraol (compound B), (2S,3S)-2,3-O-benzylidene-1,1,4,4-tetraphenyl-1,2,3,4-butanetetraol (compound C), (2R,3R)-2,3-O-benzylidene-1,1,4,4-tetraphenyl-1,2,3,4-butanetetraol (compound D), (2S,3S)-2,3-O-(1-phenylethylidene)-1,1,4,4-tetrakis(4-methoxyphenyl)-1,2,3,4-butanetetraol (compound E) and (2R,3R)-2,3-O-(1-phenylethylidene)-1,1,4,4-tetrakis(4-methoxyphenyl)-1,2,3,4-butanetetraol (compound F) as well as racemaic modifications thereof. The compound represented by the general formula (1-III) may be used in an amount of from 0.1 to 5 equivalents, preferably from 0.5 to 2 equivalents, per equivalent of the compound represented by the general formula (II). The condensation catalyst may be used in an amount of from 0.001 to 2 equivalents, preferably from 0.01 to 1.2 equivalents, per equivalent of the compound represented by the general formula (II). In some cases, the efficiency of this reaction can be elevated by adding a dehydrating agent such as Molecular Sieves 4A to the reaction system. Examples of the solvent to be used in this reaction include hydrocarbon solvents such as pentane, hexane, heptane, petroleum ether, benzene, toluene, ethylbenzene, trimethylbenzene and triisopropylbenzene, halogenated hydrocarbon solvents such as flon, ether solvents such as ether and tetrahydrofuran, acetonitrile, and mixtures thereof. The reaction temperature may range from the freezing point of the employed solvent to the boiling point thereof, preferably from $-50°$ to $30°$ C. For example, (3S,4S)-3-methoxycarbonyl-1-methylthio-4-(oxazolidin-2-on-3-yl)carbonyl-1-cyclobutene can be obtained at a high chemical yield and a high optical yield by reacting one equivalent of a compound of the general formula (II), wherein $R^2$ is a methoxycarbonyl group, A is a $CH_2CH_2$ group, Y is an oxygen atom and Z is an oxygen atom, with 1.25 equivalents of a compound of the general formula (1-III), wherein $R^1$ is a methyl group and $R^3$ is a hydrogen atom, in the presence of a condensation catalyst obtained by combining 0.10 equivalent of dichlorodiisopropoxytitanium with 0.11 equivalent of (2S,3S)-2,3-O-(1-phenylethylidene)-1,1,4,4-tetraphenyl-1,2,3,4-butanetetraol (compound A) and Molecular Sieves 4A in a solvent mixture of petroleum ether and toluene at $0°$ C. When a compound of the general formula (1-III) wherein $R^1$ is a methyl group and $R^3$ is a butyl group is used in the above reaction, (3R,4S)-2-butyl-3-methoxycarbonyl-1-methylthio-4-(oxazolidin-2-on-3-yl)carbonyl-1-cyclobutene can be obtained at a high chemical yield and a high optical yield.

Examples of the alkyl group having 1 to 5 carbon atoms represented by the group $R^1$, $R^2$ or $R^3$ in the compound of the present invention include methyl, ethyl and butyl groups, while examples of the aryl-substituted alkyl group wherein the alkyl group has 1 to 5 carbon atoms include alkyl groups having 1 to 5 carbon atoms substituted with an aromatic ring, such as a benzyl or 4-methoxybenzyl group. Examples of the protected hydroxyalkyl group having 1 to 5 carbon atoms include benzyloxymethyl, acetyloxymethyl and t-butyldiphenylsilyloxymethyl groups. Examples of the protected carboxyl group include carboxyl groups protected with an alkyl group having 1 to 5 carbon atoms, such as methoxycarbonyl and ethoxycarbonyl groups, and aralkyloxycarbonyl groups such as a benzyloxycarbonyl group. Examples of the alkoxy group having 1 to 5 carbon atoms include methoxy and allyloxy groups. Examples of the aryl-substituted alkoxy group wherein the alkoxy group has 1 to 5 carbon atoms include benzyloxy, 4-methoxybenzyloxy and t-butyldiphenylsilyloxy groups.

The compound represented by the general formula (I) may be converted into the compound represented by the general formula (VII) via the following reaction scheme (2):

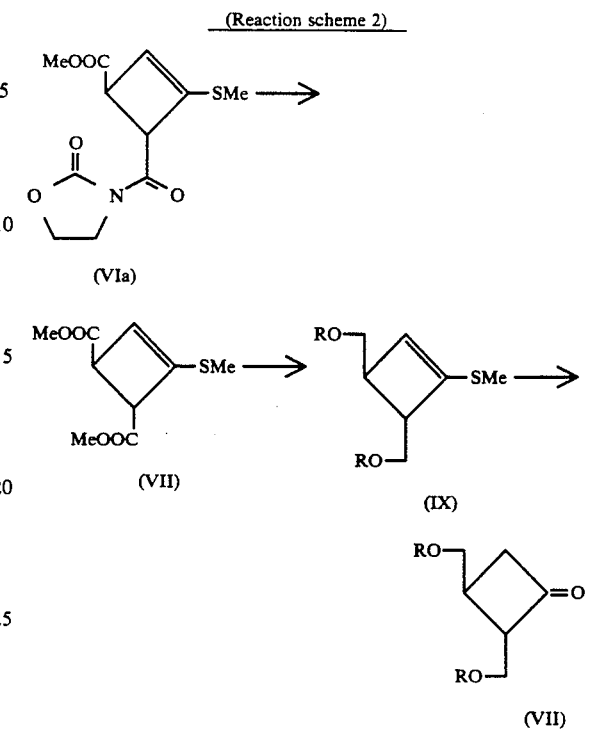

(Reaction scheme 2)

wherein R represents a protective group or a hydrogen atom.

As shown in the reaction scheme (1), the compound (VII) is an intermediate for preparing a compound having an antiviral activity. The reaction conditions for reaction scheme (2) are set forth in the Referential Example herein.

Among the compounds represented by the general formula (I), those wherein X is a

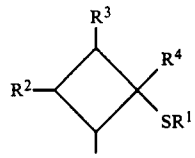

group may be obtained through the cyclocondensation of the compound represented by the above general formula (II) with a compound represented by the following general formula (2-III):

$$R^3CH=CR^4SR^1 \qquad (2\text{-III})$$

wherein $R^1$ represents an alkyl group having 1 to 5 carbon atoms or an aryl-substituted alkyl group wherein the alkyl group has 1 to 5 carbon atoms; and $R^3$ and $R^4$ independently represent each a hydrogen atom, an alkyl group having 1 to 5 carbon atoms, a protected hydroxyalkyl group having 1 to 5 carbon atoms, an alkoxy group having 1 to 5 carbon atoms or an aryl-substituted alkoxy group wherein the alkoxy group has 1 to 5 carbon atoms; or alternately $R^3$ and $R^4$ are bound together to thereby form a 3- to 30-membered carbocyclic or heterocyclic ring.

This reaction may be carried out in the same manner as the one described regarding the reaction between the compounds (II) and (1-III). The groups $R^1$ and $R^2$ in the general formula (2-111) are the same as the groups $R^1$ and $R^2$ in the above-mentioned general formula (1-III), while the groups $R^3$ and $R^4$ in the general formula (2-III) are either the same as the group $R^3$ in the above-mentioned general formula (1-111) or the groups $R^3$ and $R^4$ are bound together to thereby form a 3- to 30-membered carbocyclic or heterocyclic ring, for example, a cyclopentane ring, a cyclohexane ring, a cycloheptane ring or a cyclooctane ring. These rings may optionally have substituents. Particular examples thereof are as follows:

2-1. (+)-(1R,6S,7R,8R)-6-n-butylthio-8-methoxycarbonyl-7-(oxazolidin-2-on-3-yl)carbonylbicyclo[4.2.0]octane; and 2-2. (1S,2R,3R)-1-ethylthio-3-methoxycarbonyl-1-methyl-2-(oxazolidin-2-on-3-yl)carbonylcyclobutane.

EXAMPLE 1-1

Production of (−)-(3R,4R)-3-methoxycarbonyl-1-methylthio-4-(oxazolidin-2-on-3-yl)carbonyl-1-cyclobutene:

1.5 ml of toluene was added to 143 mg (0.605 mmol) of dichlorodiisopropoxytitanium and 352 mg (0.66 mmol) of (2R,3R)-2,3-O-(1-phenylethylidene)-1,1,4,4-tetraphenyl-1,2,3,4-butanetetraol (compound B) in an argon atmosphere and then the mixture was stirred at room temperature for 1 hour.

To 200 mg of powdery Molecular Sieves 4A, which had been dried by heating, were added 0.41 ml (0.050 mmol) of the toluene solution obtained above, 1.5 ml of toluene and 2 ml of petroleum ether (boiling point: ca. 80° C.) in an argon atmosphere. Further, 100.15 mg (0.502 mmol) of 3-[(E)-3-(methoxycarbonyl)-propenoyl]-oxazolidin-2-one was added thereto and the mixture was cooled to 0° C. To the obtained suspension was added 135 mg (1.88 mmol) of 1-methylthioacetylene dissolved in 1.5 ml of petroleum ether. Next, the mixture was stirred at the same temperature for 24 hours. Then a 0.2M phosphate buffer solution (pH 7.0) was added to the reaction mixture to thereby cease the reaction. After filtering off inorganic matters with Celite, organic matters were extracted with ethyl acetate. The extract was washed with a saturated aqueous solution of common salt and dried over anhydrous sodium sulfate. After distilling off the solvent under reduced pressure, the residue was purified by thin layer chromatography (ethyl acetate:hexane=1:1, v/v). Thus 113 mg (83%) of (−)-(3R,4R)-3-methoxycarbonyl- 1-methylthio-4-(oxazolidin-2-on-3-yl)carbonyl-1-cyclobutene was obtained. The optical purity of this compound determined by the method as will be described in Referential Example exceeded 98% ee.

$^1$H-NMR(500 MHzFT, CDCl$_3$) δ: 2.28(3 H, s), 3.72(3 H,s), 3.88(1 H, t, J=1.6 Hz), 4.05(2 H, t, J=5.6 Hz), 4.47(2 H, t, J=5.6 Hz), 4.88(1 H, d, J=1.6 Hz), 5.92(1 H, d, J=1.6 Hz). $^{13}$C-NMR (125 MHzFT, CDCl$_3$) δ: 13.6, 42.3, 45.7, 50.6, 52.0, 62.5, 123.9, 144.1, 153.2, 169.4, 171.7. IR (neat) cm$^{-1}$: 1779, 1731, 1693, HRMS CH$_{11}$H$_{13}$NO$_5$S Calcd. 271.0515. Found 271.0491. [α]$_D$ −192.6° (c 1.02, CH$_2$Cl$_2$).

EXAMPLE 1-2

Production of (−)-(3S,4R)-3-methoxycarbonyl-2-methyl-1-methylthio-4-(oxazolidin-2-on-3-yl)carbonyl-1-cyclobutene:

The procedure of Example 1-1 was repeated except that the 1-methylthioacetylene was replaced with 1-methylthio-1-propylene and that the dichlorodiisopropoxytitanium and the (2R,3R)-2,3-O-(1-phenylethylidene)-1,1,4,4-tetraphenyl-1,2,3,4-butanetetraol (compound B) were employed at an equimolar ratio. Thus (−)-(3S,4R)-3-methoxycarbonyl-2-methyl-1-methylthio-4-(oxazolidin-2-on-3-yl)-carbonyl-1-cyclobutene (72%) was obtained. The optical purity of this compound determined by the method as will be described in Referential Example exceeded 98% ee.

$^1$H-NMR(500 MHzFT, CDCl$_3$) δ: 1.83(3 H, t, J=1.7 Hz), 2.30(3 H, s), 3.63(1 H, quint, J=1.7 Hz), 3.73(3 H, s), 4.05(2 H, t, J=7.7 Hz), 4.45(2 H, t, J=7.7 Hz), 4.88(1 H, d, J=1.7 Hz). HRMS CH$_{12}$H$_{15}$NO$_5$S Calcd. 285.0672. Found 285.0676. [α]$_D$ −1.43.1° (c 1.03, CH$_2$Cl$_2$).

EXAMPLE 1-3

The following table shows examples of processes for producing the compounds of the present invention including those of Examples 1-1 and 1-2. The reaction conditions and treatment procedures employed in these examples were the same as those described in Example 1-1, unless otherwise noted. The optical purity of each product was determined by the same method as the one which will be described in Referential Example.

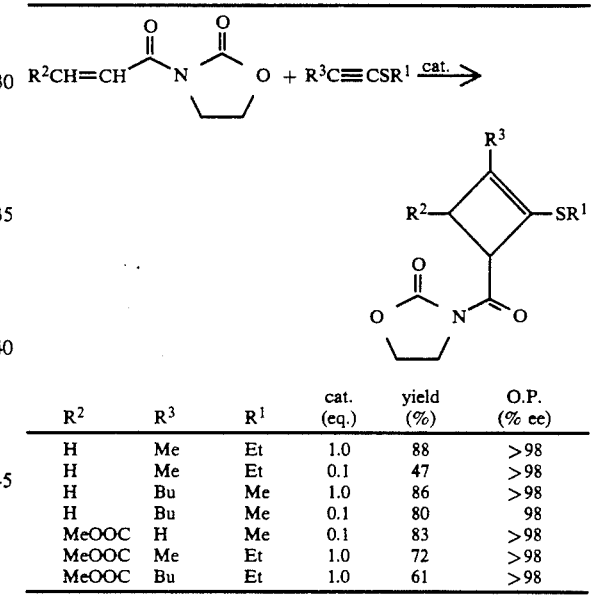

| R$^2$ | R$^3$ | R$^1$ | cat. (eq.) | yield (%) | O.P. (% ee) |
|---|---|---|---|---|---|
| H | Me | Et | 1.0 | 88 | >98 |
| H | Me | Et | 0.1 | 47 | >98 |
| H | Bu | Me | 1.0 | 86 | >98 |
| H | Bu | Me | 0.1 | 80 | 98 |
| MeOOC | H | Me | 0.1 | 83 | >98 |
| MeOOC | Me | Et | 1.0 | 72 | >98 |
| MeOOC | Bu | Et | 1.0 | 61 | >98 |

EXAMPLE 2-1

Production of (+)-(1R,6S,7R,8R)-6-n-butylthio-8-methoxycarbonyl-7-(oxazolidin-2-on-3-yl)carbonyl-bicyclo[4.2.0]octane:

4 ml of toluene was added to 111.25 mg (0.4695 mmol) of dichlorodiisopropoxytitanium and 276.50 mg (0.523 mmol) of (2R,3R)-2,3-O-(1-phenylithylidene)-1,1,4,4-tetraphenyl-1,2,3,4-butanetetraol (compound B) in an argon atmosphere and then the mixture was stirred at room temperature for 30 minutes. Further, 200 mg of powdery Molecular Sieves 4A, which had been dried by heating, 4 ml of petroleum ether (boiling point: ca. 80° C.) and 85.35 mg (0.4285 mmol) of 3-[(E)-3-(methoxycarbonyl)propenoyl]oxazolidin-2-one were added thereto and the obtained mixture was cooled to 0° C. To the obtained suspension was added 19.80 mg (0.703 mmol) of 1-n-butylthiocyclohexene dissolved in 1.5 ml of petroleum ether. Next, the mixture was stirred at 0° C. for 2 days. Then a 0.2M phosphate buffer solution (pH 7.0) was added to the reaction mixture to thereby cease the reaction. After filtering off inorganic matters with Celite, organic matters were extracted with ethyl acetate. The extract was washed with a saturated aqueous solution of common salt and dried over anhydrous sodium sulfate. After distilling off the solvent under reduced pressure, the residue was purified by thin layer chromatography (ethyl acetate:hexane=1:1, v/v). Thus 151.40 mg (96%) of (+)-(1R,6S,7R,8R)-6-n-butylthio-8-methoxycarbonyl-7-(oxazolidin-2-on-3-yl)-carbonyl-bicyclo[4.2.0]octane was obtained.

$^1$H-NMR(500 MHzFT, CDCl$_3$) δ: 0.87(3 H, t, J=2.9 Hz), 1.30–1.62(11 H, m), 1.91–1.98(1 H, m), 2.47(1 H, ddd, J=6.1, 8.4, 11.2 Hz), 2.66(1 H, dd, J=4.9, 10.0 Hz), 2.72(1 H, ddd, J=6.4, 8.4, 11.2 Hz), 3.34(1 H, t, J=10.0 Hz), 3.62(3 H, s), 3.88(1 H, ddd, J=5.0, 9.0, 11.0 Hz), 4.00(1 H, q, J=9.0 Hz), 4.12–4.40(2 H, m), 4.77(1 H, d, J=10.0 Hz). $^{13}$C-NMR(125 MHzFT, CDCl$_3$) δ: 13.5, 20.9, 21.0, 22.1, 22.5, 27.7, 29.0, 31.0, 36.6, 39.5, 42.7, 45.6, 51.2, 51.7, 61.8, 153.0, 169.7, 173.0. [α]$_D$+77.2° (c 1.13, CH$_2$Cl$_2$).

The optical purity of this product was determined by the following method. Namely, the compound was treated with magnesium methoxide in methanol at 0° C. to thereby convert it into (1R,6S,7R,8R)-6-n-butylthio-7,8-bismethoxycarbonylbicyclo[4.2.0]octane. Then it was reduced with lithium aluminum hydride in ether to thereby give (1R,6S,7R,8R)-6-n-butylthio-7,8-bishydroxymethylbicyclo[4.2.0]octane. By a conventional method using (R)-α-methoxy-α-trifluoromethylphenylacetyl chloride ((R)-MTPACl) and dimethylaminopyridine (DMAP)/pyridine (pyr), the obtained product was converted into bis-(R)-MTPA ester. Then this bis-(R)-MTPA ester was compared with another bis-(R)-MTPA ester obtained in the same manner from the racemic modification of the title compound by 500 MHz-NMR spectroscopy. Thus it was determined that the optical purity of this compound exceeded 98% ee.

EXAMPLE 2-2

(1S,2R,3R)-1-Ethylthio-3-methoxycarbonyl-1-methyl-2-(oxazolidin-2-on-3-yl)carbonylcyclobutane:

The procedure of Example 2-1 was repeated except that the 1-n-butylthiocyclohexene was replaced with 2-ethylthiopropene. Thus a mixture of (1S,2R,3R)-1-ethylthio-3-methoxycarbonyl-1-methyl-2-(oxazolidin-2-on-3-yl)carbonylcyclobutane and (1R,2R,3R)-1-ethylthio-3-methoxycarbonyl-1-methyl-2-(oxazolidin-2-on-3-yl)carbonylcyclobutane (72:28, 70%) was obtained.

$^1$H-NMR(500 MHzFT, CDCl$_3$) δ: 1.19(3×0.28 H, t, J=7.4 Hz), 1.25(8×0.72 H, t, J=7.4 Hz), 1.33(3×0.72 H, s), 1.69(3×0.28 H, s), 2.17(1×0.72 H, dd, J=1.0, 9.3 Hz), 2.33(1×0.28 H, dd, J=3.8, 8.3 Hz), 2.45–2.85(3 H, m), 3.62(1×0.72 H, q, J=9.3 Hz), 3.66(3 H, s), 3.89(1×0.28 H, dt, J=8.3, 10.2 Hz), 3.95–4.12(2 H, m), 4.37–4.46(2 H, m), 4.60(1×0.28 H, d, J=8.3 Hz), 5.00(1×0.72 H, d, J=9.3 Hz).

The relative configuration of each component of this mixture was determined by two-dimensional spectral COSY and NOESY. Further, the mixture was converted into bis-(R)-MTPA ester in the same manner as the one described in Example 2-1. Thus it was found out that the optical purity of the main component was 98.5% ee while that of the isomer thereof was 79% ee.

EXAMPLE 2-3

The following table shows examples of processes for producing the compounds of the present invention including the one of Example 2-1. The reaction conditions and treatment procedures employed in these examples were the same as those described in Example 2-1, unless otherwise noted. The optical purity of each product was determined by the same method as the one which will be described in Example 2-1.

| R$^2$ | R$^3$ + R$^4$ —(CH$_2$)$_n$— | R$^1$ | cat. (eq.) | yield (%) | O.P. (% ee) |
|---|---|---|---|---|---|
| MeOOC | n = 4 | Bu | 1.0 | 96 | >98 |
| MeOOC | n = 4 | Bu | 0.15 | 92 | >98 |
| MeOOC | n = 5 | Bu | 1.0 | 89 | >98 |
| MeOOC | n = 5 | Bu | 0.16 | 59 | >98 |
| H | n = 4 | Bu | 0.25 | 61 | >95 |

REFERENTIAL EXAMPLE (1) Production of (−)-(3R,4R)-3,4-bis(hydroxymethyl)-1-methylthio-1-cyclobutene:

In an argon atmosphere, a solution of the (−)-(3R,4R)-3-methoxycarbonyl-1-methylthio-4-(oxazolidin-2-on-3-yl)carbonyl-1-cyclobutene produced in Example 1-1 in methanol was added to an excessive amount of a solution of dimethoxymagnesium in methanol under ice-cooling. The obtained mixture was stirred at 0° C. for 15 minutes. Then a saturated aqueous solution of ammonium chloride was added to the reaction mixture, followed by extracting with ether. The ether extract was washed with a saturated aqueous solution of common salt and the solvent was distilled off under reduced pressure.

In an argon atmosphere, the residual etheric solution was slowly added to an equimolar amount of a suspension of lithium aluminum hydride in ether at 0° C. The obtained mixture was stirred at 0° C. for 2 hours. A saturated aqueous solution of sodium sulfate was added to the reaction mixture to thereby decompose the excess reducing agent. Next, anhydrous sodium sulfate was added thereto and the mixture was stirred for a while. After filtering off inorganic matters, the residue was further washed with hot isopropyl alcohol. Then the filtrate and the washing liquor were combined together. After distilling off the solvent under reduced pressure, the residue was purified by thin layer chromatography. Thus (−)-(3R,4R)-3,4-bis(hydroxymethyl)-1-methylthio-1-cyclobutene (67%) was obtained.

$^1$H-NMR(500 MHzFT, CDCl$_3$) δ: 2.28(3 H, s), 2.72(1 H, dd, J=4.9 Hz, 8.3 Hz), 2.79(1 H, dd, J=4.9 Hz, 7.9 Hz), 2.90(2 H, brs), 3.56(1 H, dd, J=8.2 Hz, 10.7 Hz), 3.67(1 H, dd, J=8.2 Hz, 11.0 Hz), 3.76(1 H, dd, J=4.9 Hz, 10.7 Hz), 3.85(1 H, dd, J=4.9 Hz, 11.0 Hz), 5.78(1 H, s). [α]$_D$−95.11° (c 0.685, CH$_2$Cl$_2$).

By a conventional method using (R)-α-methoxy-α-trifluoromethylphenylacetyl chloride ((R)-MTPACl)

and dimethylaminopyridine (DMAP)/pyridine (pyr), part of the obtained product was converted into bis-(R)-MTPA ester.

In the 500 MHz-NMR spectrum, there were observed two signals (at 2.17 and 2.18 ppm) of the methyl groups in this compound originating from the racemic modification. On the other hand, there was observed a single signal (at 2.17 ppm) of the methyl group of this substance.

These facts suggest that the optical purity of the product exceeded 98% ee.

(2) Production of (−)-(2R,3R)-2,3-bis(t-butyldiphenylsilyloxymethyl)-1-cyclobutanone:
Step 1:

68.55 mg (0.36 mmol) of (−)-(3R,4R)-3,4-bis(hydroxymethyl)-1-methylthio-1-cyclobutene, 89.80 mg (1.32 mmol) of imidazole and a catalytic amount of 4-dimethylaminomethylpyrimidine were dissolved in 3 ml of DMF. To the solution thus obtained was added 267 mg (0.97 mmol) of t-butyldiphenylsilyl chloride at room temperature, followed by stirring at room temperature for 6 hours. To the reaction mixture thus obtained was added a phosphate buffer solution (pH 7.0), followed by extracting with ether. The ether extract was washed with water and then with a saturated aqueous solution of common salt and dried over anhydrous sodium sulfate. After distilling off the solvent under reduced pressure, the residue was purified by thin layer chromatography. Thus (−)-(3R,4R)-3,4-bis(t-butyldiphenylsilyloxymethyl)-1-methylthio-1-cyclobutene was obtained quantitatively. $[\alpha]_D = -53.47°$ (c 1.00, $CH_2Cl_2$)

Step 2:

To 29.00 mg of cupric oxide (CuO) and 42.65 mg of cupric chloride ($CUCl_2$) were added 5 ml of acetone, one drop of distilled water and two drops of DMF. To the suspension thus obtained was added 44 mg of (−)-(3R,4R)-3,4-bis(t-butyldiphenylsilyloxymethyl)-1-methylthio-1-cyclobutene. After stirring the obtained mixture at 30° to 40° C. for 6 hours, 24.25 mg of cupric oxide (CuO) and 88.75 mg of cupric chloride ($CuCl_2$) were further added thereto. The obtained mixture was stirred at 30° to 40° C. for 5 hours. Then a phosphate buffer solution was added to the reaction mixture. After filtering through Celite, water was added thereto, followed by extracting with ether. The ether extract was washed with a saturated aqueous solution of common salt and dried over anhydrous sodium sulfate. After distilling off the solvent under reduced pressure, the residue was purified by thin layer chromatography. Thus 30.40 mg of (−)-(2R,3R)-2,3-bis(t-butyldiphenyl-silyloxymethyl)-1-cyclobutanone was obtained. $[\alpha]_D = -13.8°$ (c 0.608, $CH_2Cl_2$)

The physical data of this compound completely agreed with those of a compound prepared in accordance with the reaction scheme 1.

What is claimed is:

1. A cyclobutane derivative represented by the following general formula (I):

wherein X represents a group represented by the formula

(wherein $R^1$ represents a methyl group; $R^2$ represents a protected carboxyl group; $R^3$ represents hydrogen; A represents a polymethylene group having 2 carbon atoms; Y represents an oxygen atom; and Z represents an oxygen atom.

2. A cyclobutane derivative as claimed in claim 1, wherein said protected carboxyl group is a carboxyl group protected with an alkyl group having 1 to 5 carbon atoms.

3. A cyclobutane derivative as claimed in claim 1 which is represented by the following formula:

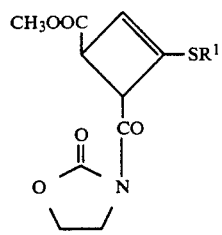

wherein $R^1$ represents a methyl group.

* * * * *